United States Patent [19]

Kimura et al.

[11] Patent Number: 5,139,565

[45] Date of Patent: Aug. 18, 1992

[54] SUBSTITUTED PYRIDINESULFONAMIDE COMPOUNDS, AND HERBICIDAL COMPOSITIONS CONTAINING THEM

[75] Inventors: Fumio Kimura, Tokyo; Takahiro Haga, Kusatsu; Nobuyuki Sakashita, Kusatsu; Shigeo Murai, Kusatsu; Yuji Nakamura, Kusatsu; Shooichi Honzawa, Kusatsu, all of Japan

[73] Assignee: Ishihara Sangyo Kaisha Ltd., Osaka, Japan

[21] Appl. No.: 658,246

[22] Filed: Feb. 20, 1991

[30] Foreign Application Priority Data

Feb. 20, 1990 [JP] Japan .................................. 2-39063

[51] Int. Cl.$^5$ .................. A01N 43/54; C07D 239/42; C07D 401/12
[52] U.S. Cl. ...................................... 71/92; 544/320; 544/331
[58] Field of Search ...................... 71/92; 544/320, 331

[56] References Cited

U.S. PATENT DOCUMENTS

| | | | |
|---|---|---|---|
| 4,435,206 | 3/1984 | Levitt | 71/92 |
| 4,456,469 | 6/1984 | Adams, Jr. | 71/93 |
| 4,522,645 | 6/1985 | Levitt | 71/93 |
| 4,544,401 | 10/1985 | Levitt | 71/92 |
| 4,605,432 | 8/1986 | Adams | 71/92 |
| 4,632,695 | 12/1986 | Schurter | 71/93 |
| 4,657,578 | 4/1987 | Thompson | 71/90 |
| 4,668,279 | 5/1987 | Rorer | 71/92 |
| 4,789,393 | 12/1988 | Hanagan | 71/92 |

FOREIGN PATENT DOCUMENTS 0232067  8/1987  European Pat. Off. .

OTHER PUBLICATIONS

Chemical Abstract, vol. 102, No. 7, Feb. 18, 1985, Columbus, Ohio, USA Lejeune, R. et al, "Preparation of the disulfide of 3-mercaptopyridine-2-sulfonamide," p. 582, Col. 1, Abstract No. 62 050z & J. Pharm. Belg. 1984, 39(4), 217-24.

Primary Examiner—John M. Ford
Attorney, Agent, or Firm—Oblon, Spivak, McClelland, Maier & Neustadt

[57] ABSTRACT

A substituted pyridinesulfonamide compound having the formula (I):

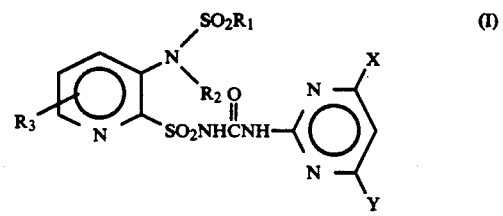

wherein $R_1$ is an alkyl group, a haloalkyl group, an alkoxyalkyl group or an alkenyl group, $R_2$ is a hydrogen atom, an alkyl group, a haloalkyl group, an alkoxyalkyl group or an alkenyl group, $R_3$ is a hydrogen atom, a halogen atom, an alkyl group, a haloalkyl group, an alkoxy group, an alkylthio group, an alkoxyalkyl group, an alkylamino group or a dialkylamino group, and each of X and Y which are independent from each other, is a halogen atom, an alkyl group, an alkoxy group or a haloalkoxy group, or salt thereof, a preparation thereof, a herbicidal composition containing it and intermediate thereof.

9 Claims, No Drawings

SUBSTITUTED PYRIDINESULFONAMIDE COMPOUNDS, AND HERBICIDAL COMPOSITIONS CONTAINING THEM

The present invention relates to novel substituted pyridinesulfonamide compounds and salts thereof, herbicidal compositions containing them as active ingredients, and a process for their production.

Heretofore, many analogue compounds have been developed as sulfonamide herbicides. For example, 2-chloro-N-[(4-methoxy-6-methyl-1,3,5-triazin-2-yl)aminocarbonyl]benzenesulfonamide (trademark: Glean®) is known as a herbicide which is safe to barley and wheat; ethyl 2-[(4-chloro-6-methoxypyrimidin-2-yl)aminocarbonylaminosulfonyl]benzoate (trademark: Classic®) is known as a herbicide which is safe to soybean; methyl 2-[(4,6-dimethoxypyrimidin-2-yl)aminocarbonylaminosulfonylmethyl]benzoate (trademark: Londax®) is known as a herbicide which is safe to paddy field rice; and methyl 2-[(4,6-dimethylpyrimidin-2-yl)aminocarbonyl-aminosulfonyl]benzoate (trademark: Oust®) is known as a non-selective herbicide.

The present inventors have conducted syntheses and researches to find sulfonamide compounds which are safe particularly to corn among crop plants, and have finally accomplished the present invention.

The present invention provides a novel substituted pyridinesulfonamide compound having the following formula (I):

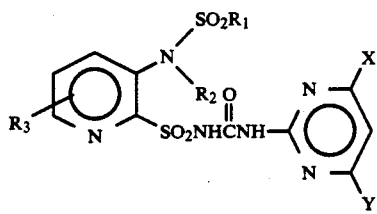

wherein $R_1$ is an alkyl group, a haloalkyl group, an alkoxyalkyl group or an alkenyl group, $R_2$ is a hydrogen atom, an alkyl group, a haloalkyl group, an alkoxyalkyl group or an alkenyl group, $R_3$ is a hydrogen atom, a halogen atom, an alkyl group, a haloalkyl group, an alkoxy group, an alkylthio group, an alkoxyalkyl group, an alkylamino group or a dialkylamino group, and each of X and Y which are independent from each other, is a halogen atom, an alkyl group, an alkoxy group or a haloalkoxy group, and its salt.

The present invention also provides a herbicidal composition comprising a terbicidally effective amount of the substituted pyridinesulfonamide compound of the formula (I) or its salt, and an agricultural adjuvant.

The present invention further provides a method for killing weeds, which comprises applying a herbicidally effective amount of the substituted pyridinesulfonamide compound of the formula (I) or its salt to the locus to be protected.

Further, the present invention provides a process for producing a substituted pyridinesulfonamide compound having the formula (I) and its salt, which comprises reacting a substituted pyridine compound having the formula (II):

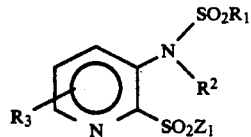

wherein $R_1$, $R_2$ and $R_3$ are as defined above, and $Z_1$ is a —$NH_2$ group, a —NCO group or a —$NHCO_2R_4$ group, wherein $R_4$ is an alkyl group or an aryl group, with a pyrimidine compound having the formula (III):

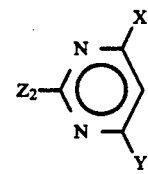

wherein X and Y are as defined above, and $Z_2$ is a —$NH_2$ group when $Z_1$ is a —NCO group or a —$NHCO_2R_4$ group, and a —NCO group or a —$NHCO_2R_4$ group, when $Z_1$ is a —$NH_2$ group, wherein $R_4$ is as defined above.

Still further, the present invention provides a substituted pyridine intermediate compound having the formula (II-1):

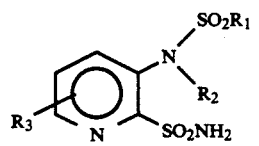

wherein $R_1$ is an alkyl group, a haloalkyl group, an alkoxyalkyl group or an alkenyl group, $R_2$ is a hydrogen atom, an alkyl group, a haloalkyl group, an alkoxyalkyl group or an alkenyl group, and $R_3$ is a hydrogen atom, a halogen atom, an alkyl group, a haloalkyl group, an alkoxy group, an alkylthio group, an alkoxyalkyl group, an alkylamino group or a dialkylamino group.

Now, the present invention will be described in further detail with reference to the preferred embodiments.

Among the compounds of the formula (I), preferred are pyridinesulfonamide compounds represented by the formula (I'):

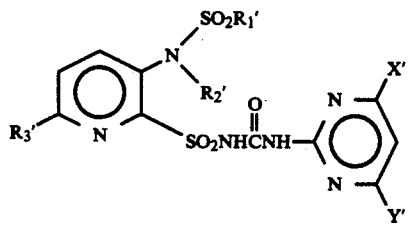

wherein $R_1'$ is an alkyl group or a haloalkyl group, $R_2'$ is an alkyl group, $R_3'$ is a hydrogen atom, a halogen atom, an alkyl group, a haloalkyl group, an alkoxy group or an alkoxyalkyl group, each of X' and Y' which are independent from each other, is a methyl group or a methoxy group, or their salts.

Among the compounds of the formula (I'), preferred are those wherein $R_1'$ is an alkyl group or a haloalkyl group, particularly an alkyl group; $R_2'$ is an alkyl group;

$R_3'$ is a hydrogen atom, a halogen atom, an alkyl group, a haloalkyl group, an alkoxy group, or an alkoxyalkyl group; each of $X'$ and $Y'$ is a methyl group or a methoxy group, and more preferred are those wherein each of $R_1'$ and $R_2'$ is a methyl group, $R_3'$ is a hydrogen atom, a halogen atom, an alkyl group or an alkoxy group, and each of $X'$ and $Y'$ which are independent from each other, is a methoxy group.

The alkyl group or the alkyl moiety in the definition of $R_1$, $R_2$, $R_3$, $X$ and $Y$ in the above formula (I) is preferably a $C_1$-$C_4$ alkyl group such as a methyl group, an ethyl group, a propyl group or a butyl group; the alkenyl group in the definition of $R_1$ and $R_2$ is preferably a $C_2$-$C_4$ alkenyl group such as a propenyl group or a butenyl group; and the halogen atom in the definition of $R_1$, $R_2$, $R_3$, $X$ and $Y$ may be a fluorine atom, a chlorine atom, a bromine atom or an iodine atom.

The salt of the compound of the present invention may, for example, be an alkali metal salt such as a sodium salt or a potassium salt, an alkaline earth metal salt such as a magnesium salt or a calcium salt, or a quaternary ammonium salt such as a methylamine salt, a dimethylamine salt or a triethylamine salt.

The novel substituted pyridinesulfonamide compound of the above formula (I) can be prepared by e.g. the following methods (A) to (D):

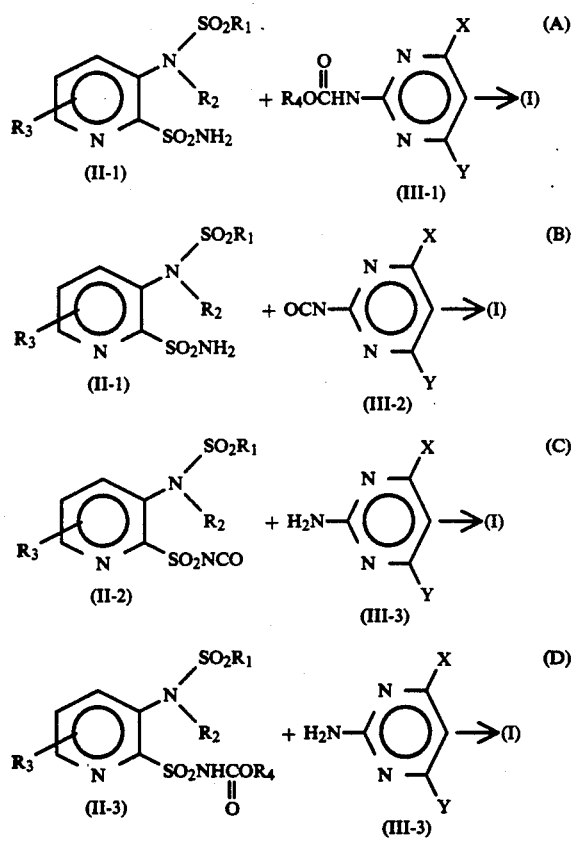

In the reaction formulas for the methods (A) to (D), $R_1$ is an alkyl group, a haloalkyl group, an alkoxyalkyl group or an alkenyl group, $R_2$ is a hydrogen atom, an alkyl group, a haloalkyl group, an alkoxyalkyl group or an alkenyl group, $R_3$ is a hydrogen atom, a halogen atom, an alkyl group, a haloalkyl group, an alkoxy group, an alkylthio group, an alkoxyalkyl group, an alkylamino group or a dialkylamino group, and each of $X$ and $Y$ which are independent from each other, is a methyl group or a methoxy group, and $R_4$ is an alkyl group or an aryl group.

The alkyl group for $R_4$ may be the same alkyl group as mentioned with respect to $R_1$, $R_2$ and $R_3$, and the aryl group for $R_4$ may be a phenyl group, a phenyl group substituted by a chlorine atom, a phenyl group substituted by a methyl group, or a naphthyl group.

The reaction (A) is conducted in the presence of a base, and the reactions (B), (C) and (D) may also be conducted in the presence of a base as the case requires. As the base, a tertiary amine such as triethylamine, or 1,8-diazabicyclo[5.4.0]-7-undecene may be used.

The reactions (A), (B), (C) and (D) may be conducted in the presence of a solvent as the case requires. The solvent may be an aromatic hydrocarbon such as benzene, toluene, xylene or chlorobenzene; a cyclic or non-cyclic aliphatic hydrocarbon such as chloroform, carbon tetrachloride, methylene chloride, dichloroethane, trichloroethane, hexane or cyclohexane; an ether such as diethyl ether, dioxane or tetrahydrofuran; a nitrile such as acetonitrile, propionitrile or acrylonitrile; an ester such as methyl acetate or ethyl acetate; or an aprotic polar solvent such as dimethylsulfoxide or sulforane.

The reaction (A) is conducted usually at a reaction temperature of from $-20°$ to $+100°$ C., preferably from $0°$ to $40°$ C. for a reaction time of from 0.01 to 24 hours, preferably from 0.1 to 1.5 hours; the reaction (B) is conducted usually at a reaction temperature of from 0 to $150°$ C. for a reaction time of from 0.1 to 24 hours; the reaction (C) is conducted usually at a reaction temperature of from $0°$ to $150°$ C. for a reaction time of from 0.1 to 24 hours; and the reaction (D) is conducted usually at a reaction temperature of $-20°$ to $+150°$ C., preferably from 50 to $110°$ C. for a reaction time of from 0.1 to 24 hours.

The compound of the formula (II-1) used as the starting material for the reactions (A) and (B) can be prepared by e.g. the following methods (E), (F) and (G):

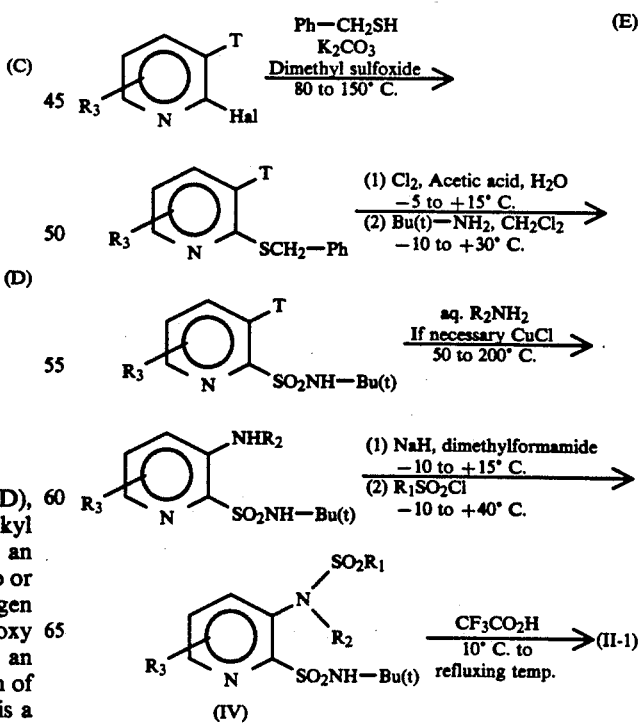

-continued

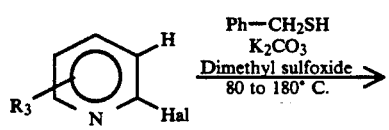 (F)

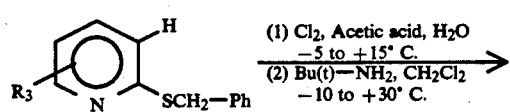

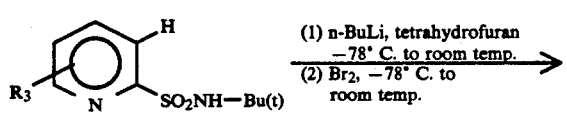

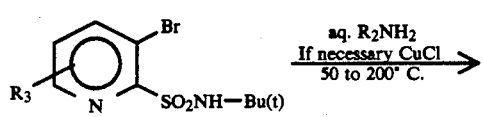

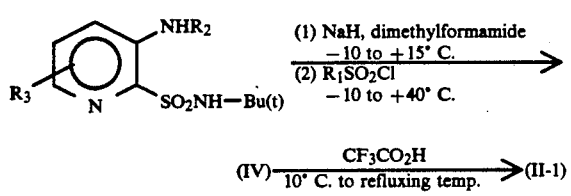

(IV) $\xrightarrow[\text{10° C. to refluxing temp.}]{\text{CF}_3\text{CO}_2\text{H}}$ (II-1)

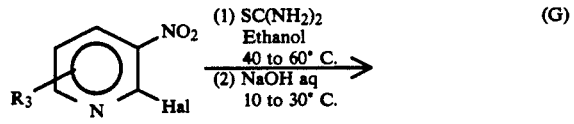 (G)

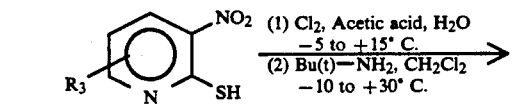

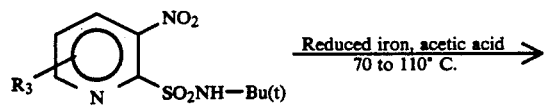

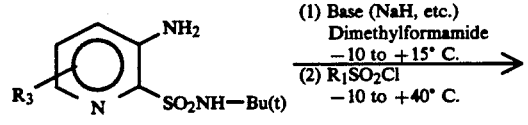

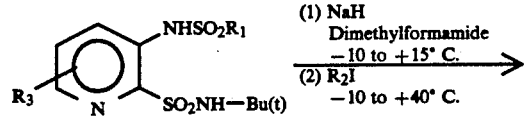

(VI) $\xrightarrow[\text{10° C. to refluxing temp.}]{\text{CF}_3\text{CO}_2\text{H}}$ (II-1)

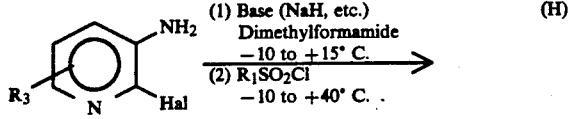 (H)

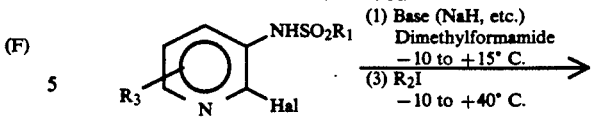

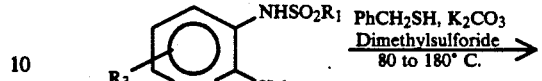

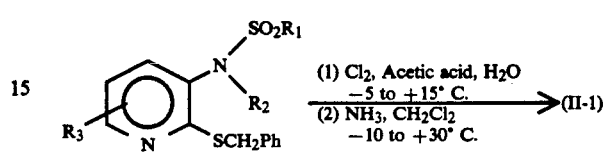 (II-1)

In the reaction formulas (E), (F), (G) and (H), $R_1$, $R_2$ and $R_3$ are as defined above, T is a chlorine atom or a bromine atom, and Hal is a fluorine atom, a chlorine atom, a bromine atom or an iodine atom. Further, Ph represents a phenyl group, Bu(t) represents a tert-butyl group, and aq. represents an aqueous solution.

Among the compounds of the formula (II-1), those wherein $R_3$ is an alkoxy group:

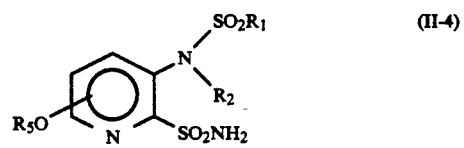 (II-4)

wherein $R_1$ and $R_2$ are as defined above, and $R_5$ is a $C_1$-$C_4$ alkyl group, can be prepared also by e.g. the following method (I).

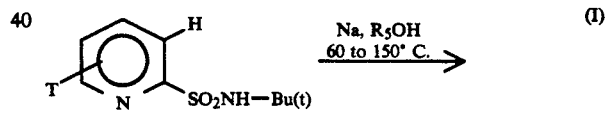 (I)

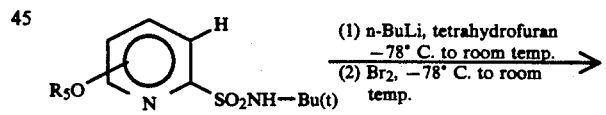

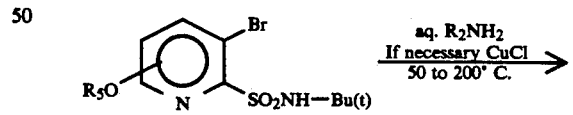

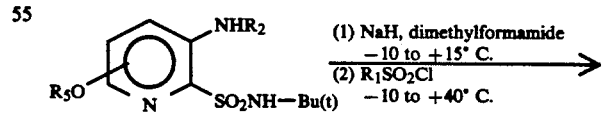

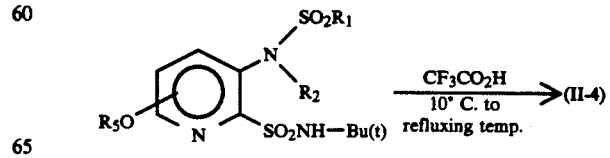 (II-4)

In the reaction formulas, $R_1$, $R_2$, $R_5$, T, Bu(t) and aq. are as defined above.

Further, the compounds of the formula (II 2) in the reaction (C) can be prepared by e.g. the following method (J), and the compounds of the formula (II-3) in the reaction (D) can be prepared by e.g. the following method (K).

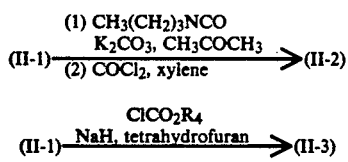

In the reaction formula (K), R$_4$ is as defined above.

The substituted pyridinesulfonamide compound of the formula (I) can be also produced by another method as follows.

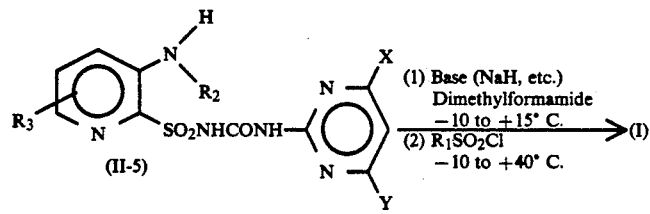

The raw material of the formula (II-5) in the reaction formula (L) can be produced, for example, by the method (M).

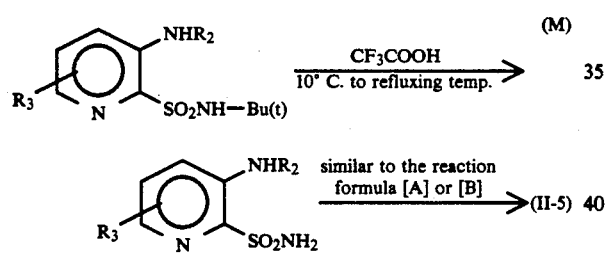

R$_1$, R$_2$, R$_3$, X, Y and Bu(t) in the reaction formula are as defined above.

The reaction conditions for the respective reactions (E) to (M) such as the reaction temperatures, the reaction times and the solvents and alkaline substances to be used as the case requires, may suitably be selected from the reaction conditions commonly employed in similar reactions, unless otherwise specified.

The salts of the substituted pyridinesulfonamide compounds of the present invention can readily be prepared by usual methods.

The intermediate compounds of the formula (II-1) are novel compounds, and their typical examples will be given in Table 1.

TABLE 1

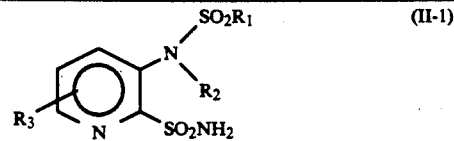

| Intermediate No. | R$_1$ | R$_2$ | R$_3$ | Melting point (°C.) |
|---|---|---|---|---|
| 1 | CH$_3$ | CH$_3$ | H | 179–183 |

TABLE 1-continued

| Intermediate No. | R$_1$ | R$_2$ | R$_3$ | Melting point (°C.) |
|---|---|---|---|---|
| 2 | C$_2$H$_5$ | CH$_3$ | H | 149–150 |
| 3 | CH$_3$ | C$_2$H$_5$ | H | 186–187.5 |
| 4 | CH$_3$ | n-C$_3$H$_7$ | H | — |
| 5 | CH$_3$ | H | H | — |
| 6 | CH$_3$ | CH$_3$ | 6-OCH$_3$ | 149–152 |
| 7 | CH$_3$ | CH$_3$ | 6-OC$_2$H$_5$ | 155–158 |
| 8 | CH$_3$ | CH$_3$ | 6-F | 179–182 |
| 9 | CH$_3$ | CH$_3$ | 6-Cl | — |
| 10 | CH$_3$ | CH$_3$ | 6-Br | — |
| 11 | CH$_3$ | CH$_3$ | 6-CH$_3$ | 129.5–132 |
| 12 | CF$_3$ | CH$_3$ | H | — |
| 13 | C$_2$H$_5$ | CH$_3$ | 6-OC$_2$H$_5$ | 128–130 |
| 14 | CH$_3$ | CH$_3$ | 6-CF$_3$ | — |
| 15 | CH$_3$ | CH$_3$ | 6-N(CH$_3$)$_2$ | — |
| 16 | CH$_3$ | CH$_3$ | 6-SCH$_3$ | — |
| 17 | CH$_3$ | CH$_3$ | 6-CH$_2$OCH$_3$ | — |
| 18 | CH$_3$ | CH$_3$ | 6-C$_2$H$_5$ | — |
| 19 | CH$_3$ | CH$_3$ | 5-CF$_3$ | 145–148 |
| 20 | CH$_3$ | CH$_3$ | 5-CH$_3$ | — |
| 21 | CH$_3$ | CH$_3$ | 5-OCH$_3$ | — |
| 22 | CH$_3$ | CH$_3$ | 5-Cl | — |
| 23 | CH$_3$ | CH$_2$CF$_3$ | H | — |
| 24 | CH$_2$CF$_3$ | CH$_3$ | H | — |
| 25 | CH$_2$CH$_2$OCH$_3$ | CH$_3$ | H | — |
| 26 | CH=CH$_2$ | CH$_3$ | H | — |

Among the compounds of the formula (II-1), preferred are compounds represented by the formula (II-1'):

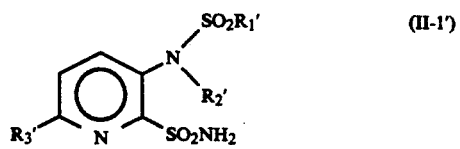

wherein R$_1$' is an alkyl group or a haloalkyl group, R$_2$' is an alkyl group, R$_3$' is a hydrogen atom, a halogen atom, an alkyl group, a haloalkyl group, an alkoxy group or an alkoxyalkyl group.

Among the compounds of the formula (II-1'), preferred are those wherein R$_1$' is an alkyl group, and more preferred are those wherein each of R$_1$' and R$_2$' is a methyl group, and R$_3$' is a hydrogen atom, a halogen atom, an alkyl group or an alkoxy group.

Now, Synthesis Examples for the preparation of the compounds of the present invention will be described.

SYNTHESIS EXAMPLE 1

Preparation of N-[(4,6-dimethoxypyrimidin-2-yl)aminocarbonyl]-3-(N'-methyl-N'-methylsulfonylamino)-2pyridinesulfonamide (Compound No. 1 as described hereinafter)

(1) 10 g of 2,3-dichloropyridine, 11.2 g of anhydrous potassium carbonate and 100 ml of dimethylsulfoxide were mixed to obtain a suspension. To this suspension, 10 ml of a dimethylsulfoxide solution of 10.1 g of benzyl mercaptan was dropwise added over a period of about 20 minutes at 110° C. Then, the mixture was reacted at a temperature of from 120 to 130° C. for about 1.5 hours. Thereafter, the reaction product was put into water and extracted with methylene chloride. The methylene chloride layer was dried over anhydrous sodium sulfate. Then, methylene chloride was distilled off under reduced pressure, and the obtained residue was purified by silica gel column chromatography to obtain 12.5 g of oily 2-benzylthio-3-chloropyridine.

(2) Into 100 ml of a 50% acetic acid aqueous solution containing 12.1 g of 2-benzylthio-3-chloropyridine obtained in the above step (1), chlorine gas was introduced at a temperature of from 0 to 5° C., and the reaction was terminated at the stage where excess chlorine gas started to appear. The reaction solution was put into 200 g of ice and extracted with methylene chloride. The extract was washed with 600 ml of water and then cooled to 0° C., and 20.2 g of tert-butyl amine was dropwise added thereto at a temperature of from 0 to 10° C. After completion of the dropwise addition, the mixture was reacted at room temperature for about one hour. The reaction solution was put into water and extracted with methylene chloride, and then dried over anhydrous sodium sulfate. Then, methylene chloride was distilled off under reduced pressure. The obtained residue was purified by silica gel column chromatography to obtain 10.1 g of N-tert-butyl-3-chloro-2-pyridinesulfonamide having a melting point of from 138° to 141° C.

(3) 3.0 g of N-tert-butyl-3-chloro-2-pyridinesulfonamide obtained in the above step (2), 60 ml of a 25% methylamine aqueous solution and 0.1 g of cuprous chloride were charged into a 100 ml autoclave and reacted at 150° C. for about 13.5 hours. After completion of the reaction, the reaction solution was cooled and put into 100 ml of water. The resulting crystals were collected by filtration and dried under reduced pressure to obtain 1.7 g of N-tert-butyl-3-methylamino-2-pyridinesulfonamide having a melting point of from 230° to 232° C.

(4) To a mixture comprising 0.7 g of N-tert-butyl-3-methylamino-2-pyridinesulfonamide obtained in the above step (3) and 20 ml of dimethylformamide, 0.253 g of 60% sodium hydride was added in divided portions at a temperature of from 0 to 5° C. The mixture was reacted at 0° C. for about 30 minutes, and then 10 ml of a dimethylformamide solution of 0.563 g of methanesulfonyl chloride was dropwise added at a temperature of from 0° to 10° C. over a period of about 15 minutes. After the dropwise addition, the mixture was further reacted at room temperature for about 30 minutes. The reaction product was put into water and after adjusting the pH to be weakly acidic with concentrated hydrochloric acid, extracted with methylene chloride. The extract was dried over anhydrous sodium sulfate. Then, methylene chloride was distilled off under reduced pressure, and the residue was purified by silica gel column chromatography to obtain 0.66 g of N-tert-butyl-3-(N'-methyl-N'-methylsulfonylamino)-2-pyridinesulfonamide as highly viscous oil. This compound had the following NMR values. NMR(CDCl₃)

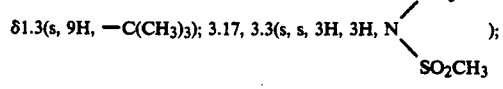

5.46(s, 1H, NH); 7.33–7.60(dd, 1H),; 7.83–7.97(dd, 1H); 8.5–8.6(dd, 1H)

(5) 0.66 g of N-tert-butyl 3-(N'-methyl-N'-methylsulfonylamino)-2-pyridinesulfonamide obtained in the above step (4) and 5 ml of trifluoroacetic acid were mixed and reacted for about 2 hours under reflux. After completion of the reaction, trifluoroacetic acid was distilled off under reduced pressure from the reaction product. The residue was crystallized by means of ethyl acetate and n-hexane, and the resulting crystals were collected by filtration and dried to obtain 0.44 g of 3-(N-methyl-N-methylsulfonylamino)-2-pyridinesulfonamide (the above-mentioned intermediate No. 1) having a melting point of from 179 to 183° C. This compound had the following NMR values. NMR(DMSO-d₆):

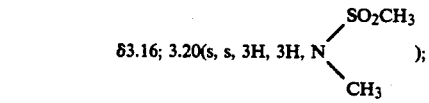

7.54(s, 2H, SO₂NH₂); 7.72–7.75(dd, 1H); 8.03–8.05(dd, 1H), 8.64–8.66(dd, 1H)

(6) 0.265 g of 3-(N-methyl-N-methylsulfonylamino)-2-pyridinesulfonamide obtained in the above step (5) and 0.276 g of 2-phenoxycarbonylamino-4,6-dimethoxypyrimidine were added to 10 ml of dry acetonitrile. To this suspension, 0.152 g of 1,8-diazabicyclo[5.4.0]-7-undecene was further added, and the mixture was reacted at room temperature for about 30 minutes. After completion of the reaction, the reaction solution was put into 200 ml of water and weakly acidified with concentrated hydrochloric acid. The resulting crystals were collected by filtration and dried under reduced pressure to obtain 0.420 g of the desired product (Compound No. 1) having a melting point of from 181° to 184° C. This compound had the following NMR values. NMR(CDCl₃):

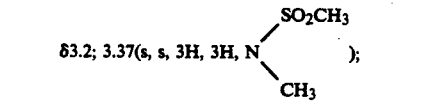

3.94(s, 6H, OCH₃); 5.80(s, 1H); 7.55–7.58(dd, 1H), 7.98–8.00(dd, 1H), 8.54–8.55(dd, 1H), 12.88(s, NH)

SYNTHESIS EXAMPLE 2

Preparation of N-[(4,6-dimethoxypyrimidin-2-yl)aminocarbonyl]-3-(N'-methyl-N'-methylsulfonylamino)-6-methyl-2-pyridinesulfonamide (Compound No. 12 as described hereinafter)

(1) 12.8 g of 2-chloro-6-methylpyridine, 18 g of anhydrous potassium carbonate and 100 ml of dimethylsulfoxide were mixed to obtain a suspension. This suspension was preliminarily heated to a temperature of from 120° to 130° C., and 10 ml of a dimethylsulfoxide solution of 18.6 g of benzyl mercaptan was dropwise added thereto over a period of about 30 minutes. Then, the mixture was reacted at 150° C. for about one hour. Thereafter, the reaction solution was cooled, then put into water and extracted with methylene chloride. The methylene chloride layer was dried over anhydrous sodium sulfate, and then methylene chloride was distilled off under reduced pressure. The obtained residue was purified by silica gel column chromatography to obtain 7.53 g of oily 2-benzylthio-6-methylpyridine.

(2) To 140 ml of a 50% acetic acid aqueous solution of 7.5 g of 2-benzylthio-6-methylpyridine obtained in the above step (1), chlorine gas was introduced at a temperature of from 0° to 5° C., and the reaction was terminated at the stage where excess chlorine started to appear. After purging the excess chlorine gas by dry nitrogen gas, the reaction solution was put into 500 ml of ice water and extracted with 500 ml of methylene chloride. The methylene chloride layer was washed with ice water and then cooled to a temperature of from 0° to 5° C., and tert-butylamine was dropwise added thereto at the same temperature until the methylene chloride solution became alkaline. After completion of the dropwise addition, the mixture was reacted at room temperature for about one hour. After completion of the reaction, the reaction solution was put into water, then extracted with methylene chloride and dried over anhydrous sodium sulfate. Then, methylene chloride was distilled off under reduced pressure. To the obtained residue, ethyl acetate and n-hexane were added. The resulting crystals were collected by filtration to obtain 3.5 g of N-tert-butyl-6-methyl-2-pyridinesulfonamide having a melting point of from 120.5° to 123° C. On the other hand, the filtrate was concentrated, and the residue thereby obtained was purified by silica gel column chromatography to further obtain 1.45 g of the above sulfonamide.

(3) To 60 ml of a tetrahydrofuran solution of 4.6 g of N-tert-butyl-6-methyl-2-pyridinesulfonamide obtained in the above step (2), 26.8 ml of n-butyl lithium having a (concentration of 1.57 mol/l was dropwise added at −78° C. over a period of about 15 minutes. At that time, heat was generated to bring the temperature to the maximum of −40° C. Thereafter, the mixture was reacted at -78° C. for about 15 minutes, and then 4.8 g of bromine was added over a period of about 10 minutes at a temperature of from −78° to −40° C. Then, the temperature was gradually raised to room temperature, and the mixture was reacted at room temperature for about 30 minutes. After completion of the reaction, the reaction solution was put into water, acidified with concentrated hydrochloric acid, then extracted with methylene chloride and dried over anhydrous sodium sulfate. Then, methylene chloride was distilled off under reduced pressure. The obtained residue was purified by silica gel column chromatography to obtain 2.14 g of 3-bromo-N-tert-butyl-6-methyl-2-pyridinesulfonamide having a melting point of from 123° to 128° C.

(4) 2.0 g of 3-bromo-N-tert-butyl-6-methyl-2-pyridinesulfonamide obtained in the above step (3) and 20 ml of a 30% methylamine aqueous solution were charged into a 50 ml autoclave and reacted at 150° C. for about 2 hours. After completion of the reaction, the reaction solution was cooled, then put into 100 ml of water and extracted with methylene chloride. The methylene chloride layer was dried over anhydrous sodium sulfate, and then methylene chloride was distilled off under reduced pressure. To the obtained residue, small amounts of methylene chloride and n-hexane were added. The resulting crystals were collected by filtration to obtain 285 mg of N-tert-butyl-6-methyl-3-methylamino-2-pyridinesulfonamide having a melting point of from 145° to 156° C. On the other hand, the filtrate was concentrated, and the residue was purified by silica gel column chromatography to further obtain 315 mg of the above sulfonamide.

(5) To 15 ml of a dimethylformamide solution of 590 mg of N-tert-butyl-6-methyl-3-methylamino-2-pyridinesulfonamide obtained in the above step (4), 193 mg of 60% sodium hydride was added at a temperature of from 0 to 5° C., and the mixture was reacted for 15 minutes. Thereafter, 1 ml of a dimethylformamide solution of 551 mg of methanesulfonyl chloride was dropwise added at a temperature of from 0° to 5° C., and the mixture was reacted for about 30 minutes and further reacted at a temperature of from 15° to 20° C. for about 30 minutes. After completion of the reaction, the reaction solution was put into 200 ml of water and extracted with methylene chloride. The methylene chloride layer was washed with water and dried over anhydrous sodium sulfate. Then, methylene chloride was distilled off under reduced pressure. The obtained residue was purified by silica gel column chromatography to obtain 680 mg of oily N-tert-butyl-3-(N'-methyl-N -methylsulfonylamino)-6-methyl-2-pyridinesulfonamide.

(6) Into 10 ml of trifluoroacetic acid, 680 mg of N-tert-butyl-3-(N'-methyl-N'-methylsulfonylamino)-6-methyl-2-pyridinesulfonamide obtained in the above step (5) was added, and the mixture was reacted at a temperature of not higher than 40° C. for about 30 minutes and then further reacted under reflux for 30 minutes. After completion of the reaction, trifluoroacetic acid was distilled off under reduced pressure from the reaction product. To the obtained residue, small amounts of ethyl acetate and n-hexane were added for crystallization. The resulting crystals were collected by filtration and dried under reduced pressure to obtain 380 mg of 3-(N-methyl-N-methylsulfonylamino)-6-methyl-2-pyridinesulfonamide (the above-mentioned intermediate No. 11) having a melting point of from 129.5° to 132° C.

(7) 200 mg of 3-(N-methyl-N-methylsulfonylamino)-6-methyl-2-pyridinesulfonamide obtained in the above step (6) and 208 mg of 2-phenoxycarbonylamino-4,6-dimethoxypyrimidine were added to 10 ml of dry acetonitrile to obtain a suspension. To the suspension, 120 mg of 1,8-diazabicyclo[5.4.0]-7-undecene was added, and the mixture was reacted at room temperature for about 15 minutes. After completion of the reaction, the reaction product was put into 50 ml of water and weakly acidified with concentrated hydrochloric acid. The resulting crystals were collected by filtration and dried under reduced pressure to obtain 310 mg of the desired product (Compound No. 12) having a melting point of from 162° to 168° C.

SYNTHESIS EXAMPLE 3

Preparation of N-[(4,6-dimethoxypyrimidin-2-yl)aminocarbonyl]-3-(N'-methyl-N'-methylsulfonylamino)-2l-pyridinesulfonamide (Compound No. 1 as described hereinafter)

(1) A mixture of 3.50 g of N-tert-butyl-3-methylamino-2-pyridinesulfonamide and 20 ml of trifluoroacetic acid was reacted at about 50° C. for 2 hours. Thereafter, the reaction product was distilled off under a reduced pressure to obtain a residue. Ethyl acetate and n-hexane were added thereto. The resulting crystals were filtered to obtain 2.41 g of 3-methylamino 2-pyridinesulfonamide. This compound had the following NMR values.

NMR(aceton-d$_6$): δ3.0(s,3H,CH$_3$); 6.6(s,2H,SO$_2$NH$_2$); 7.4(dd,1H); 7.5(d,1H); 7.9(d,1H)

(2) 2.41 g of 3-methylamino-2-pyridinesulfonamide obtained in the above step (1), 3.54 g of phenyl (4,6-dimethoxypyrimidin-2-yl)carbamate and 30 ml of acetonitrile were mixed and 1.96 g of 1,8-diazabicyclo[5.4.0]-7-undecene was added thereto under an icy-cooling. The mixture was reacted at room temperature for 2 hours. After completion of the reaction, the reaction product was put into 500 ml of water and the resulting crystals were filtered. The filtrate was weakly acidified with hydrochloric acid. The resulting crystals were filtered, washed and dried to obtain 3.56 g of N-[(4,6-dimethoxypyrimidin-2-yl)aminocarbonyl]-3-methylamino-2-pyridinesulfonamide having a melting point of from 145° to 147° C.

(3) The N-[(4,6-dimethoxypyrimidin-2-yl)aminocarbonyl]-3-methylamino-2-pyridinesulfonamide obtained in the above step (2) can be derived into the desired product (Compound No. 1) by using a similar processes to those of said Synthesis Example 1(4).

Now, typical examples of the compound of the present invention represented by the formula (I) will be given in Table 2.

TABLE 2

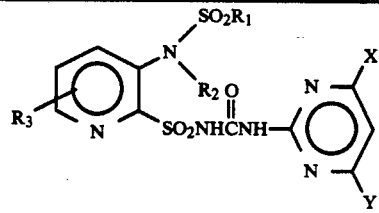

| Compound No. | R$_1$ | R$_2$ | R$_3$ | X | Y | Salt | Melting point (°C.) |
|---|---|---|---|---|---|---|---|
| 1 | CH$_3$ | CH$_3$ | H | OCH$_3$ | OCH$_3$ | — | 181–184 |
| 2 | C$_2$H$_5$ | CH$_3$ | H | OCH$_3$ | OCH$_3$ | — | 162–164.5 |
| 3 | CH$_3$ | H | H | OCH$_3$ | OCH$_3$ | — | — |
| 4 | CH$_3$ | CH$_3$ | H | OCH$_3$ | CH$_3$ | — | 176–179 |
| 5 | CH$_3$ | CH$_3$ | H | CH$_3$ | CH$_3$ | — | 185–188 |
| 6 | CH$_3$ | C$_2$H$_5$ | H | OCH$_3$ | OCH$_3$ | — | 177–182 |
| 7 | CH$_3$ | C$_2$H$_5$ | H | CH$_3$ | CH$_3$ | — | 190–193 |
| 8 | CH$_3$ | CH$_3$ | 6-OCH$_3$ | OCH$_3$ | OCH$_3$ | — | 182–186 |
| 9 | CH$_3$ | CH$_3$ | 6-OC$_2$H$_5$ | OCH$_3$ | OCH$_3$ | — | 188–192 |
| 10 | CH$_3$ | CH$_3$ | 6-OC$_2$H$_5$ | CH$_3$ | CH$_3$ | — | 205–209 |
| 11 | CH$_3$ | CH$_3$ | 6-Cl | OCH$_3$ | OCH$_3$ | — | — |
| 12 | CH$_3$ | CH$_3$ | 6-CH$_3$ | OCH$_3$ | OCH$_3$ | — | 162–168 |
| 13 | CF$_3$ | H | H | OCH$_3$ | OCH$_3$ | — | — |
| 14 | CF$_3$ | CH$_3$ | H | OCH$_3$ | OCH$_3$ | — | — |
| 15 | CH$_3$ | CH$_3$ | 6-F | OCH$_3$ | OCH$_3$ | — | 147–150 |
| 16 | C$_2$H$_5$ | CH$_3$ | 6-OC$_2$H$_5$ | OCH$_3$ | OCH$_3$ | — | 161–163 |
| 17 | CH$_3$ | CH$_3$ | H | OCH$_3$ | OCH$_3$ | Na | 199–204 |
| 18 | CH$_3$ | CH$_3$ | 6-CF$_3$ | OCH$_3$ | OCH$_3$ | — | — |
| 19 | CH$_3$ | CH$_3$ | 6-N(CH$_3$)$_2$ | OCH$_3$ | OCH$_3$ | — | — |
| 20 | CH$_3$ | CH$_3$ | 6-SCH$_3$ | OCH$_3$ | OCH$_3$ | — | — |
| 21 | CH$_3$ | CH$_3$ | 6-CH$_2$OCH$_3$ | OCH$_3$ | OCH$_3$ | — | — |
| 22 | CH$_3$ | CH$_3$ | 6-C$_2$H$_5$ | OCH$_3$ | OCH$_3$ | — | — |
| 23 | CH$_3$ | CH$_3$ | 5-CF$_3$ | OCH$_3$ | OCH$_3$ | — | 117–121 |
| 24 | CH$_3$ | CH$_3$ | 5-CH$_3$ | OCH$_3$ | OCH$_3$ | — | — |
| 25 | CH$_3$ | CH$_3$ | 5-OCH$_3$ | OCH$_3$ | OCH$_3$ | — | — |
| 26 | CH$_3$ | CH$_3$ | 5-Cl | OCH$_3$ | OCH$_3$ | — | — |
| 27 | CH$_3$ | CH$_3$ | H | Cl | OCH$_3$ | — | 173–176 |
| 28 | CH$_3$ | CH$_3$ | H | OCHF$_2$ | OCH$_3$ | — | Oil |
| 29 | CH$_3$ | CH$_3$ | 6-F | Cl | OCH$_3$ | — | 158–161 |
| 30 | CH$_3$ | CH$_3$ | 6-OCH$_3$ | Cl | OCH$_3$ | — | 186–190 |
| 31 | CH$_3$ | CH$_3$ | 6-CH$_3$ | Cl | OCH$_3$ | — | 173–176 |
| 32 | CH$_3$ | CH$_3$ | H | OCH$_2$CH$_3$ | OCH$_2$CH$_3$ | — | 187–190 |
| 33 | CH$_3$ | CH$_3$ | H | OCHF$_2$ | OCHF$_2$ | — | Oil |
| 34 | CH$_3$ | CH$_2$CF$_3$ | H | OCH$_3$ | OCH$_3$ | — | — |
| 35 | CH$_2$CF$_3$ | CH$_3$ | H | OCH$_3$ | OCH$_3$ | — | — |
| 36 | CH$_2$CH$_2$OCH$_3$ | CH$_3$ | H | OCH$_3$ | OCH$_3$ | — | — |
| 37 | CH=CH$_2$ | CH$_3$ | H | OCH$_3$ | OCH$_3$ | — | — |

As will be evident from the Test Examples given hereinafter, the substituted pyridinesulfonamide compounds of the present invention exhibit safety to corn and at the same time exhibit a wide herbicidal spectrum including gramineous weeds at a low dose.

The herbicidal compositions of the present invention may be applied to various places including agricultural fields such as upland fields, orchards, mulberry fields and non-agricultural fields such as forests, farm roads, open grounds and factory sites.

Further, the manner of application may suitably be selected from the soil treatments and foliage treatments. For the application of the herbicidal compositions of the present invention, the active ingredients are usually mixed with various agricultural adjuvants such as a carrier, a diluent, a solvent, an emulsifier, a spreader and a surfactant, as the case requires, and may be formulated in various formulations such as granules, water dispersible granules, wettable powders, emulsifiable concentrates, water-soluble powders or soluble concentrates. The weight ratio of the active ingredient to the agricultural adjuvants is usually from 1:99 to 90:10, preferably from 5:95 to 80:20. The suitable dose of the active ingredient can not simply be determined since it may vary depending upon the weather condition, the soil condition, the type of the formulation, the types of the weeds to be controlled, the season for the application, etc. However, it is usual that the effective dose is within a range of from 0.005 to 50 g/a, preferably from 0.01 to 10 g/a, more preferably from 0.05 to 5 g/a.

The herbicidal compositions of the present invention may be used in combination with or together with other agricultural chemicals, agricultural adjuvants or phytotoxicity-reducing agents. In such a combination, they may exhibit even better effects or activities. In a case when they are used in combination with or together with other herbicides, the following compounds may be mentioned, for example, as the active ingredients of such other herbicides. In some cases, synergistic effects may be obtained.

3,6-dichloro-2-methoxybenzoic acid;
2,5-dichloro-3-aminobenzoic acid;
(2,4-dichlorophenoxy)acetic acid;
(4-chloro-2-methylphenoxy)acetic acid;
2-chloro-4,6-bis(ethylamino)-1,3,5-triazine;
2-chloro-4-ethylamino-6-isopropylamino-1,3,5-triazine;
2-(4-chloro-6-ethylamino-1,3,5-triazin-2-ylamino)-2-methylpropionitrile;
2-ethylamino-4-isopropylamino-6-methylthio-1,3,5-triazine;
2-chloro-2',6'-diethyl-N-(methoxymethyl)acetanilide;
2-chloro-6'-ethyl-N-(2-methoxy-1-methylethyl)aceto-o-toluidide;
2-chloro-N-isopropylacetanilide;
2-chloro-N,N-di-2-propenylacetamide;
S-ethyl dipropylthiocarbamate;
S-ethyl diisobutylthiocarbamate;
S-propyl dipropylthiocarbamate;
N-(1-ethylpropyl)-2,6-dinitro-3,4-xylidine;
α,α,α-trifluoro-2,6-dinitro-N,N-dipropyl-p-toluidine;
2-(3,5-dichlorophenyl)-2-(2,2,2-trichloroethyl)oxirane;
3-isopropyl-(1H)-benzo-2,1,3-thiadiazin-4-one-2,2-dioxide;
3-(3,4-dichlorophenyl)-1-methoxy-1-methylurea;
3,5-dibromo-4-hydroxybenzonitrile;
2,6-dibromo-4-cyanophenyl octanoate;
2-chloro-4-trifluoromethylphenyl-3-ethoxy-4-nitrophenyl ether;
4-hydroxy-3,5-diiodobenzonitrile;
4-cyano-2,6-diiodophenyl octanoate;
4-chloro-2-oxobenzothiazol-3-yl acetic acid; methyl 3-[[[[(4-methoxy-6-methyl-1,3,5-triazin-2yl)amino]-carbonyl]amino]sulfonyl]-2-thiophene carboxylate;
N,N-dimethyl-2-[3-(4,6-dimethoxypyrimidin-2-yl)ureidosulfonyl]nicotinamide;
N-[4,6-dimethoxypyrimidin-2-yl)aminocarbonyl]-2-(2-methyl-2H-tetrabenzol-5-yl)benzenesulfonamide;
N-[(4-chloro-6-methoxypyrimidin-2-yl)aminocarbonyl]-2-(2-methyl-2H-tetrazol-5-yl)benzenesulfonamide;
3-ethylaminosulfonyl-N-[(4,6-dimethoxypyrimidin-2-yl)aminocarbonyl]-pyridine-2-sulfonamide;
N-[(4,6-dimethoxypyrimidin-2-yl)aminocarbonyl]-3-propylsulfonylpyridine-2-sulfonamide;
N-[(4,6-dimethoxypyrimidin-2-yl)aminocarbonyl]-3-(ethylsulfonyl)-2-pyridinesulfonamide;
3-[4,6-bis(difluoromethoxy)pyrimidin-2-yl]-1-(2-methoxycarbonylphenylsulfonyl)urea.
O-(6-chloro-3-phenyl-4-pyridazinyl)-S-octylthiocarbamate Now, Test Examples of the herbicidal compositions of the present invention will be described.

TEST EXAMPLE

A pot of 1/1,500 are (are=100 m$^2$) was filled with upland field soil, and seeds of various plants were sown. Then, when the test plants reached to predetermined leaf stages (corn (*Zea mays*): 2.2–4.3 leaf stage, wheat (*Triticum*): 2.3–3.0 leaf stage, soy bean (*Glycine max*): primary leaf stage to 1.5-leaf stage, cotton (*Gossypium*): cotyledon stage to 1.2-leaf stage, rice (*Oryza sativa*): 1.5–3.7 leaf stage, cocklebur (*Xanthium strumarium*): 1.8–3.5 leaf stage, morningglory (*Ipomoea purpuea*): 0.5–2.5 leaf stage, barnyard grass (*Echinochloa crus-galli*): 1.7–4.0 leaf stage, slender amaranth (*Amaranthus viridis*): 0.1–2.5 leaf stage, prickly sida (*Sida spinosa*): 0.1–2.5 leaf stage), a wettable powder of the compound of the present invention was weighed in a predetermined amount and diluted with water in an amount of 5 l per are. To this aqueous solution, an agricultural spreader was further added in an amount to bring the concentration to 0.2%, followed by foliage treatment by means of a small size spray. Seventeen to thirtyfive days after the treatment, the growth of the respective plants were visually inspected, and the degree of growth inhibition was evaluated on a scale of 10 grades in which 10 indicates that the plant was completely killed and 1 indicates no effects, as shown in Table 3 below.

TABLE 3

| Compound No. | Amount of active ingredient (g/a) | Degree of growth inhibition | | | | | | | | | | Evaluation date |
|---|---|---|---|---|---|---|---|---|---|---|---|---|
| | | ZE | TR | GL | GO | OR | XA | IP | EC | AM | SI | |
| 1 | 0.3 | 5 | — | 10 | 9 | 9 | 10 | 9 | 9 | 10 | 9 | 17th day |
| | 0.16 | 4 | — | 10 | 9 | 10 | 10 | 9 | 10 | 10 | 9 | |
| | 0.08 | 4 | — | 9 | 9 | 10 | 9 | 9 | 10 | 10 | 7 | |
| 2 | 1.25 | 3 | 7 | 9 | — | 8 | 10 | 9 | 10 | 9 | 6 | 23rd day |
| 4 | 0.63 | 2 | 7 | 9 | 6 | 7 | 10 | 8 | 8 | 10 | 7 | 22nd day |
| | 0.31 | 1 | 6 | 9 | 5 | 6 | 9 | 7 | 7 | 9 | 6 | |
| 8 | 1.25 | 5 | 6 | 10 | 8 | 6 | 10 | 8 | 8 | 10 | 7 | 26th day |
| 9 | 1.25 | 3 | 6 | 10 | 8 | 7 | 10 | 10 | 6 | 9 | 6 | 24th day |

TABLE 3-continued

| Compound No. | Amount of active ingredient (g/a) | ZE | TR | GL | GO | OR | XA | IP | EC | AM | SI | Evaluation date |
|---|---|---|---|---|---|---|---|---|---|---|---|---|
| 12 | 1.25 | 3 | 10 | 10 | 9 | 10 | 10 | 10 | 10 | 10 | 8 | 25th day |
|  | 0.31 | 3 | 8 | 10 | 7 | 8 | 10 | 10 | 9 | 10 | 8 |  |
| 15 | 0.31 | 4 | 6 | 9 | 7 | 6 | 9 | 10 | 7 | 10 | 7 | 22nd day |
| 16 | 1.25 | 1 | 3 | 5 | 7 | 3 | — | 7 | 3 | 9 | 7 | 23rd day |
| 17 | 0.31 | 3 | 10 | 9 | 8 | 8 | 10 | 10 | 9 | 10 | 9 | 27th day |
|  | 0.08 | 2 | 7 | 9 | 7 | 7 | 10 | 10 | 6 | 10 | 8 |  |
| 23 | 5.0 | 1 | 6 | 4 | 3 | 6 | 9 | 6 | 6 | 7 | 6 | 25rd day |
| 27 | 1.25 | 2 | — | 5 | 7 | 10 | 10 | 10 | 10 | 10 | 5 | 35th day |
|  | 0.31 | 3 | — | 3 | 7 | 10 | 10 | 10 | 10 | 10 | 5 |  |
| 28 | 1.25 | 3 | — | 9 | 7 | 8 | 10 | 10 | 9 | 10 | 5 | 28th day |
| 29 | 5.0 | 2 | — | 9 | 8 | 8 | 10 | 10 | 6 | 10 | 6 | 28th day |
|  | 1.25 | 1 | — | 7 | 7 | 4 | 10 | 10 | 5 | 10 | 5 |  |
| 30 | 5.0 | 1 | — | 10 | 8 | 5 | — | 9 | 7 | 8 | 7 | 23th day |
|  | 1.25 | 1 | — | 8 | 7 | 3 | 8 | 9 | 5 | 7 | 5 |  |

Now, Formulation Examples of the herbicidal composition of the present invention will be described.

FORMULATION EXAMPLE 1

| (1) Water-soluble starch | 55 parts by weight |
|---|---|
| (2) Sodium lignin sulfonate | 5 parts by weight |
| (3) Compound No. 17 | 40 parts by weight |

The above components are mixed to obtain a water-soluble powder.

FORMULATION EXAMPLE 2

| (1) Kaoline | 78 parts by weight |
|---|---|
| (2) Lavelin S (tradename, manufactured by Dai-ichi Kogyo Seiyaku Co., Ltd.) | 2 parts by weight |
| (3) Sorpol 5039 (tradename, manufactured by Toho Chemical Industry Co., Ltd.) | 5 parts by weight |
| (4) Carplex (tradename, manufactured by Shionogi & Co., Ltd.) | 15 parts by weight |

A mixture of components (1) to (4) is mixed with compound No. 4 in a weight ratio of 9:1 to obtain a wettable powder.

FORMULATION EXAMPLE 3

| (1) Diatomaceous earth | 63 parts by weight |
|---|---|
| (2) Dikssol W-66 (tradename, manufactured by Dai-ichi Kogyo Seiyaku Co., Ltd.) | 5 parts by weight |
| (3) Dikssol W-0913 (tradename, manufactured by Dai-ichi Kogyo Seiyaku Co., Ltd.) | 2 parts by weight |
| (4) Compound No. 12 | 30 parts by weight |

The above components are mixed to obtain a wettable powder.

FORMULATION EXAMPLE 4

| (1) Hi-Filler No. 10 (tradename, manufactured by Matsumura Sangyo K.K.) | 33 parts by weight |
|---|---|
| (2) Sorpol 5050 (tradename, manufactured by Toho Chemical Industry Co., Ltd.) | 3 parts by weight |
| (3) Sorpol 5073 (tradename, manufactured by Toho Chemical Industry Co., Ltd.) | 4 parts by weight |
| (4) Compound No. 15 | 60 parts by weight |

The above components are mixed to obtain a wettable powder.

FORMULATION EXAMPLE 5

| (1) Compound No. 16 | 4 parts by weight |
|---|---|
| (2) Corn oil | 79 parts by weight |
| (3) Sorpol 3815 (tradename, manufactured by Toho Chemical Industry Co., Ltd.) | 15 parts by weight |
| (4) Organic bentonite | 2 parts by weight |

The above components (1) to (4) are uniformly mixed and pulverized by a Dyno mill (manufactured by Willey et Barhofen Co.) to obtain a suspension composition.

FORMULATION EXAMPLE 6

| (1) Compound No. 1 | 75 parts by weight |
|---|---|
| (2) Demol EP powder (tradename, manufactured by Kao Corporation) | 13.5 parts by weight |
| (3) sodium chloride | 10 parts by weight |
| (4) dextrin | 0.5 part by weight |
| (5) TP-89121 (tradename, manufactured by Takemoto Oil & Fat Co., Ltd.) |  |

The above compounds (1) to (5l) are introduced into a mixing and refining machine with high speedy and 20% of water is added thereto. They are uniformly mixed, granulated and dried to obtain a water dispersible granules.

We claim:

1. A substituted pyridinesulfonamide compound having the formula (I):

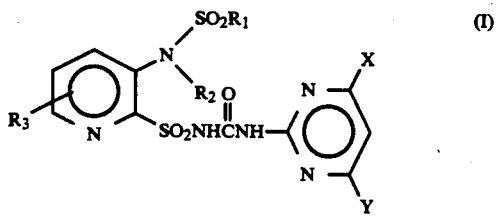

wherein $R_1$ is an alkyl group, a haloalkyl group, an alkoxyalkyl group, the alkyl moieties containing from 1-4 carbon atoms, or a $C_2$-$C_4$l-alkenyl group, $R_2$ is a hydrogen atom, an alkyl group, a haloalkyl group, an alkoxyalkyl group, the alkyl moieties containing from 1-4 carbon atoms, or $C_2$-$C_4$ 1 alkenyl group, $R_3$ is a hydrogen atom, a halogen atom, an alkyl group, a haloalkyl group, an alkoxy group, an alkylthio group, an alkoxyalkyl group, an alkylamino group or a dialkylamino group, the alkyl moieties containing from 1-4 carbon atoms, and each of X and Y which are independent from each other, is a halogen atom, an alkyl group, an alkoxy group or a haloalkoxy group, the alkyl moieties containing from 1-4 carbon atoms, or its salt.

2. The compound according to claim 1, which is a substituted pyridinesulfonamide compound having the formula (I'):

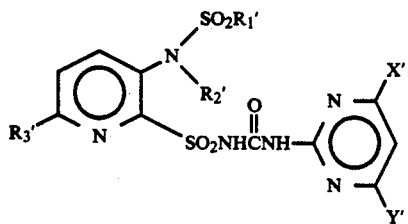

wherein $R_1'$ is an alkyl group or a haloalkyl group, $R_2'$ is an alkyl group, the alkyl moieties containing from 1-4 carbon atoms, $R_3'$ is a hydrogen atom, a halogen atom, an alkyl group, a haloalkyl group, an alkoxy group or an alkoxyalkyl group, the alkylmoieties containing from 1-4 carbon atoms, each of X' and Y' which are independent rom each other, is a methyl group or a methoxy group, or its salt.

3. The compound according to claim 2, wherein $R_1'$ is a $C_1$-$C_4$-alkyl group, $R_3'$ is a hydrogen atom, a halogen atom, an alkyl group or an alkoxy group, the alkyl moieties containing from 1-4 carbon atoms, and each of X' and Y' is a methoxy group.

4. The compound according to claim 2, wherein each of $R_1'$ and $R_2'$ is a methyl group, $R_3'$ is a hydrogen atom, a halogen atom, an alkyl group or an alkoxy group, the alkyl moieties containing from 1-4 carbon atoms, and each of X' and Y' is a methoxy group.

5. A herbicidal composition comprising a herbicidally effective amount of the substituted pyridinesulfonamide compound of the formula (I) as defined in claim 1 or its salt, and an agricultural adjuvant.

6. The herbicidal composition according to claim 5, wherein $R_1$ is an alkyl group or a haloalkyl group, the alkyl moieties containing from 1-4 carbon atoms, $R_2$ is a $C_1$-$C_4$-alkyl group, $R_3$ is a hydrogen atom, a halogen atom, an alkyl group, a haloalkyl group, an alkoxy group or an alkoxyalkyl group, the alkyl moieties containing from 1-4 carbon atoms, and each of X and Y which are independent from each other, is a methyl group or a methoxy group.

7. The herbicidal composition according to claim 5 or 6, wherein the proportion of the compound of the formula (I) or its salt to the agricultural adjuvant is within a range of from 1:99 to 990:10.

8. A method for killing weeds, which comprises applying the substituted pyridinesulfonamide compound of the formula (I) as defined in claim 1 or its salt to a corn field at a dose of from 0.005 to 50 g/a.

9. The method according to claim 8, wherein $R_1$ is an alkyl group or a haloalkyl group, the alkyl moieties containing from 1-4 carbon atoms, $R_2$ is a $C_1$-$C_4$-alkyl group, $R_3$ is a hydrogen atom, a halogen atom, an alkyl group, a haloalkyl group, an alkoxy group or an alkoxyalkyl group, the alkyl moieties containing from 1-4 carbon atoms, and each of X and Y which are independent from each other, is a methyl group or a methoxy group.

* * * * *